United States Patent
Morriss

(10) Patent No.: US 11,946,093 B2
(45) Date of Patent: Apr. 2, 2024

(54) ENZYME ADDITION TO OMEGA 3 FERMENTATION BROTH FOR THE REDUCTION OF OLIGOSACCHARIDES THROUGH STERILIZED DEXTROSE SOLUTION

(71) Applicant: Archer Daniels Midland Company, Decatur, IL (US)

(72) Inventor: Jill M. Morriss, Blue Mound, IL (US)

(73) Assignee: ARCHER-DANIELS-MIDLAND COMPANY, Decatur, IL (US)

( * ) Notice: Subject to any disclaimer, the term of this patent is extended or adjusted under 35 U.S.C. 154(b) by 356 days.

(21) Appl. No.: 17/286,306

(22) PCT Filed: Oct. 16, 2019

(86) PCT No.: PCT/US2019/056456
§ 371 (c)(1),
(2) Date: Apr. 16, 2021

(87) PCT Pub. No.: WO2020/081637
PCT Pub. Date: Apr. 23, 2020

(65) Prior Publication Data
US 2023/0242949 A1      Aug. 3, 2023

Related U.S. Application Data

(60) Provisional application No. 62/746,847, filed on Oct. 17, 2018.

(51) Int. Cl.
| | | |
|---|---|---|
| *C12P 7/6427* | (2022.01) | |
| *C12N 1/12* | (2006.01) | |
| *C12N 9/34* | (2006.01) | |
| *C12P 7/649* | (2022.01) | |
| *C12R 1/885* | (2006.01) | |
| *C12R 1/89* | (2006.01) | |

(52) U.S. Cl.
CPC .............. *C12P 7/6427* (2013.01); *C12N 1/12* (2013.01); *C12N 9/2428* (2013.01); *C12P 7/649* (2013.01); *C12N 2500/34* (2013.01); *C12N 2523/00* (2013.01); *C12R 2001/885* (2021.05); *C12R 2001/89* (2021.05); *C12Y 302/01003* (2013.01)

(58) Field of Classification Search
CPC .......... C12P 7/6427; C12P 7/649; C12N 1/12; C12N 9/2428; C12N 2500/34; C12N 2523/00; C12R 2001/885; C12R 2001/89; C12Y 302/01003
See application file for complete search history.

(56) References Cited

FOREIGN PATENT DOCUMENTS

| WO | WO-2015065978 A1 * | 5/2015 | ................ C12F 3/02 |
| WO | WO-2018120574 A1 * | 7/2018 | ............... C11B 1/06 |

OTHER PUBLICATIONS

Bassiri "Preparation of media" U Penn, accessed from https://www.sas.upenn.edu/LabManuals/biol275/Table_of_Contents_files/2-PreparationOfMedia.pdf on May 30, 2023 (Year: 2023).*
Buffers, Common. "Media, and Stock Solutions." Current Protocols in Human Genetics; Willey: Hoboken, NJ, USA (2000). (Year: 2000).*
Dias (Maltulose formation during saccharification of starch. Starch-Stärke 39.2 (1987): 64-66)). (Year: 1987).*
DHA (retrieved from https://www.mountsinai.org/health-library/supplement/docosahexaenoic-acid-dha#:~:text=Docosahexaenoic%20acid%20(DHA)%20is%20an,fatty%20fish%2C%20such%20as%20salmon on Oct. 23, 2023). (Year: 2023).*

* cited by examiner

*Primary Examiner* — Robert J Yamasaki
*Assistant Examiner* — Trevor Kane
(74) *Attorney, Agent, or Firm* — Andrew F. Nilles

(57) ABSTRACT

A method and modified fermentation intermediate are disclosed for the production of polyunsaturated fatty acid (PUFA). The method comprises heat sterilizing a fermentation medium comprising dextrose to produce a heat sterilized fermentation medium, wherein the heat sterilizing converts at least a portion of the dextrose to DP2+ sugars. The method comprises combining the heat sterilized fermentation medium with an enzyme capable of converting DP2+ sugars to dextrose, thereby producing a modified heat sterilized fermentation medium comprising more dextrose and less DP+ 2 sugars than without combining the medium with the enzyme. The modified heat sterilized fermentation intermediate may be placed in contact with a microorganism to produce PUFA, wherein the microorganism is capable of utilizing dextrose to produce PUFA.

18 Claims, No Drawings

US 11,946,093 B2

ENZYME ADDITION TO OMEGA 3 FERMENTATION BROTH FOR THE REDUCTION OF OLIGOSACCHARIDES THROUGH STERILIZED DEXTROSE SOLUTION

CROSS-REFERENCE TO RELATED APPLICATIONS

This application is a national stage entry of International Application No. PCT/US2019/056456, filed Oct. 16, 2019, which itself claims priority to U.S. Provisional Patent Application No. 62/746,847, filed Oct. 17, 2018, each of the contents of the entirety of which are incorporated by this reference.

FIELD OF THE INVENTION

The present invention relates to a fermentation process using a microorganism of algal origin.

BACKGROUND

Omega-3 fatty acids are polyunsaturated fatty acids (PUFAs). There are three types of omega-3 fatty acids involved in human physiology—α-linolenic acid (ALA) found in plant oils, and eicosapentaenoic acid (EPA) and docosahexaenoic acid (DHA), both commonly found in marine oils. DHA methyl ester is an ester version of the free acid, which is less water soluble than DHA, but is generally more amendable for formulation of fatty acid-containing diets and dietary supplements. FAME is an acronym for fatty acid methyl esters, which includes DHA methyl ester.

Microorganisms of algal origin, e.g., algae, are available in vast quantities. Dextrose is the D-isomer of glucose. Glucose is commonly manufactured from cornstarch by hydrolysis via pressurized steaming at controlled pH in a jet followed by enzymatic depolymerization.

Producing useful products, such as omega-3 fatty acids (e.g., DHA), from dextrose using algal microorganisms via conventional fermentation techniques has been limited due to lower than expected yields of resulting product.

It has been reported that the enzyme trehalase converts trehalose (a type of sugar that is not readily fermented to ethanol) to glucose, which is easily fermentable. Bioenergy International, Biofuels & Oils, Feb. 22, 2017, "Novozymes launches advanced enzymes targeting DP2 sugars in ethanol plants." The same document states that trehalose makes up a significant part of the so-called DP2 peak (two-sugar chains such as trehalose), a measure of residual sugar in an ethanol plant. The document states that the more DP2 an ethanol plant can convert; the more ethanol it will produce from the same feedstock.

There remains an ongoing need to improve fermentation processes to produce omega-3 fatty acids such as DHA using dextrose and algae sources as commercially viable alternatives to other techniques.

SUMMARY

Aspects of the invention are associated with the discovery of approaches to produce a heat sterilized fermentation medium comprising more dextrose and less DP2+ sugars than conventional techniques.

Aspects of the invention reside in a fermentation process comprising heat sterilizing a fermentation medium comprising dextrose, wherein the heat sterilizing converts at least a portion of the dextrose to DP2+ sugars. The process comprises combining an enzyme with the fermentation medium, wherein the enzyme is capable of breaking down the DP2+ sugars in the fermentation medium and converting the DP2+ sugars to dextrose, thereby producing a modified sterilized fermentation medium comprising more dextrose and less DP2+ sugars than without combining the enzyme with the fermentation medium. The process comprising placing a microorganism in contact with the modified sterilized fermentation medium, wherein the microorganism consumes the dextrose, thereby producing omega-3 fatty acid. In an embodiment, the microorganism is of an algal origin. In an embodiment, the omega-3 fatty acid that is produced comprises docosahexaenoic acid (DHA).

In an aspect, a modified fermentation medium is generated by the process of a) heat sterilizing a fermentation medium comprising dextrose to produce a heat sterilized fermentation medium, wherein the heat sterilizing converts at least a portion of the dextrose to DP2+ sugars; and b) combining the heat sterilized fermentation medium with an enzyme capable of breaking down and converting DP2+ sugars to dextrose, whereby at least a portion of the DP2+ sugars produced during heat sterilizing is converted to dextrose, thereby producing a modified heat sterilized fermentation medium comprising more dextrose and less DP+2 sugars than without combining the medium with the enzyme, wherein the enzyme is an alpha-glucosidase enzyme (also referred herein as α-glucosidase enzyme).

These and other aspects and associated advantages will become apparent from the following Detailed Description.

DETAILED DESCRIPTION

Embodiments of the invention relate to methods and compositions for, as well as end products resulting from, heat sterilizing a fermentation medium comprising dextrose, and enzymatic reaction of the sterilized fermentation medium comprising at least a portion of DP2+ sugars formed during heat sterilizing step.

In an embodiment, the fermentation medium may comprise a commercially available dextrose or dextrose monohydrate. An example of a commercially available dextrose monohydrate is Clintose® Dextrose VF (available from Archer Daniels Midland Company, Chicago, IL).

In an embodiment, the enzyme may be an alpha-glucosidase enzyme preparation derived from *Trichoderma reesei* expressing the gene encoding alpha-glucosidase from *Aspergillus niger* (e.g., the enzyme identified in GRAS Notification No. GRN 315). According to GRAS Notification 315: the systematic name of the principle enzyme activity is 1,4-α-D-glucan: 1,4-α-D-glucan (D-glucose) 6-α-D-glucosyltransferase. Other names used are Oligoglucan-branching glycosyltransferase; 1,4-α-D-glucan 6-α-D-glucosyltransferase; T-enzyme; D-glucosyltransferase, and alpha-glucosidase. The enzyme catalyzes both hydrolytic and transfer reactions on incubation with α-D-glucooligosaccharides. Transfer occurs most frequently to HO-6, producing isomaltose from D-glucose, and panose from maltose. Alpha-glucosidase can also transfer to the HO-2 or HO-3 of D-glucose to form kojibiose or nigerose, or back to HO-4 to form maltose. The action on maltose produces equimolar concentration of panose and glucose. The EC number of the enzyme is 2.4.1.24, and the CAS number is 9030-12-0.

It has been discovered that the continuous sterilization of dextrose, such as 97DE dextrose or dextrose monohydrate, such as Clintose® Dextrose VF, can cause the formation of oligosaccharides. It has been discovered that the heat that the dextrose is exposed to during sterilization has a tendency to polymerize some dextrose causing a drop in the concentration of dextrose and an increase in the DP2s and DP3s. It has been discovered that conventional fermentation techniques are limited due to low yields because when dextrose is sterilized using heat prior to being placed into contact with algal microorganisms, some dextrose is converted to oligosaccharides having a degree of polymerization of two or more (DP2+), and at least some algal microorganisms are not capable of consuming DP2+ sugars during the fermentation process. For example, the algal strain used in the fermentation, e.g., a Schizochytrium sp., cannot utilize the higher sugars, and end up contributing to non-FAME solids in the broth. The non-FAME solids in the broth can cause problems in drying and downstream processing of the product. The addition of an alpha-glucosidase enzyme reduces these oligosaccharides to dextrose and makes the sugar available to the algal strain. The addition of an alpha-glucosidase enzyme also reduces the residual sugars in biomass, thereby providing the additional benefit of facilitating downstream processing, including less browning and stickiness of the dried product.

Test results are shown in the Table below. The testing showed that an alpha-glucosidase enzyme addition reduces the DP2 and DP3 concentrations in the fermentation broth and reduces the total solids (carbohydrate related solids). The testing also showed that an alpha-glucosidase enzyme addition has a positive effect on the FAME, DHA production, and DHA yield from fermentation of a fermentation medium comprising dextrose. The testing also showed that late stage addition of one dose of an alpha-glucosidase enzyme was as effective in reducing accumulated DP2s and DP3s as three additions starting in the $24^{th}$ hour. Testing also showed that, on average, an alpha-glucosidase enzyme addition decreases the foaming in the fermentation broth, and therefore, on average, reduces the need for anti-foam usage.

Methods

Control fermentations were run without an α-glucosidase enzyme addition (identified as "Control Fermentations" in the Table), and other fermentations were run with an α-glucosidase enzyme addition (identified as "Test Fermentations" in the Table). The dextrose feed for all fermentations was 97DE. The fermentations were performed using a 7.5 L New Brunswick™ Eppendorf Bio-Flo 310 fermenter/bioreactor system, and a batch complex medium consisting of a nitrogen source, corn steep liquor, and salts. The batch complex medium was placed in the fermenter/bioreactor system. The dextrose feed, consisting of 97DE dextrose, was placed in a 5-liter glass carboy. The fermenter/bioreactor system and the glass carboy were autoclaved for 60 minutes at 121° C. and a pressure of 15 pounds per square inch (psi). After heat sterilization and cooling of the dextrose feed and the batch complex medium, fed-batch fermentations were performed in the fermenter/bioreactor system using a microalgae Schizochytrium sp. and the heat sterilized batch complex medium. Each fermentation was conducted with an elapsed fermentation time (EFT) of 72 hours. The fermentation broth was collected and analyzed for dextrose and DP2-10, total solids, and FAME/DHA.

For fermentations run with an α-glucosidase enzyme, an α-glucosidase enzyme was diluted 1:1 with deionized water and sterile filtered. The diluted α-glucosidase enzyme was distributed to syringes for injection into a fermenter at specific time points in the fermentation. The time of injection and the frequency of injection varied in the fermentations. For example, in some of the experiments below, a single injection of 4.5 ml of diluted enzyme was made at one point in time during fermentation. In Test Fermentations having a single injection of 4.5 ml of diluted enzyme, the injection was made at EFT=50 hours. In Test Fermentation DHA1505 (Fermenter C3) having three injections, consisting of 1.4 ml of diluted enzyme in each injection, the injections were made at EFT=24, 36, and 60 hours. In Test Fermentation DHA1509 (Fermenter C4) having three injections, consisting of 1.5 ml of diluted enzyme in each injection, the injections were made at EFT=24, 48, and 50 hours. In Test Fermentation DHA1510 (Fermenter C1) having three injections, consisting of 1.5 ml of diluted enzyme in each injection, the injections were made at EFT=24, 36, and 50 hours. In Test Fermentation DHA1511 (Fermenter C3) having three injections, consisting of 1.5 ml of diluted enzyme in each injection, the injections were made at, or EFT=24, 36, and 50 hours.

Results

The addition of α-glucosidase enzyme, whether it is added in one aliquot or three aliquots, reduced the DP2s and DP3s in the fermentation broth by an average of 81% and 44% respectively, compared to control fermentations without the addition of α-glucosidase enzyme.

Further, with the addition of α-glucosidase enzyme, the reduction of the residual sugars resulted in an average 6.4% reduction of total solids compared to control fermentations without the addition of α-glucosidase enzyme. Also, with the addition of α-glucosidase enzyme, an average 5.6% increase was seen in the % FAME/100 g biomass and 4.7% increase of the DHA in biomass % compared to control fermentations without the addition of α-glucosidase enzyme. Further, with the addition of α-glucosidase enzyme, an average 5.6% increase in total grams of DHA were produced per fermentation compared to control fermentations without the addition of α-glucosidase enzyme.

Antifoam usage and foaming may also be reduced by the addition of α-glucosidase enzyme. The Table shows an average of all fermentations with the addition of α-glucosidase enzyme compared to control fermentations without the addition of α-glucosidase enzyme. As shown in the Table, the addition of α-glucosidase enzyme on average results in less foam while using less antifoam agent than without the addition of α-glucosidase enzyme. Compare average antifoam agent usage of 20.0 grams and resulting average foam out of 2.0 for the control fermentations without the addition of α-glucosidase enzyme versus average antifoam agent usage of 15.3 and resulting average foam out of for fermentations with the addition of α-glucosidase enzyme (wherein foam out was qualitatively observed, and observed foam out of "++" is assigned a value of 2.0, less observed foam out of "+" is assigned a value of 1.0, and observed no foam out "−" is assigned a value of 0.0).

As demonstrated above, alpha-glucosidase enzyme addition to the omega-3 fermentation process provides benefits such as a reduction of unutilized sugars in the broth and biomass. Use of alpha-glucosidase enzyme during the fermentation process may provide an increase in FAME in the biomass, and a reduced foaming and antifoam usage. Use of the alpha-glucosidase enzyme was on average more effective in reducing antifoam usage when it was added in three aliquots. This may be due to the first aliquot addition being added earlier in the fermentation that a single addition later in the fermentation. The alpha-glucosidase enzyme treated broth dried easier and did not come off the dryer in sheets, unlike the untreated broth. Without alpha-glucosidase enzyme addition to the fermentation process, the color of the biomass appeared to have a gold color. With alpha-glucosidase enzyme addition to the fermentation process, the color of the biomass appeared to have a gray color, not gold. The gold color is believed to be a result of caramelized residual sugars.

The crude oil from the alpha-glucosidase enzyme-treated batch was reported to be of very good quality (oxidative and color) and refined very well. The quality of the finished refined, bleached and deodorized ("RBD") oil was high, which indicates that the enzyme treatment had no negative effects on oil refining.

As can be seen from the above results, significant increased yields of polyunsaturated fatty acid (PUFA) can be produced under the disclosed reaction conditions and with the described reaction mixture components. It is expected that process optimization, based on the teachings herein, can be conducted to increase yields of polyunsaturated fatty acid (PUFA), including omega-3 fatty acids (e.g., DHA).

While the aspects described herein have been discussed with respect to specific examples including various modes of carrying out aspects of the disclosure, those skilled in the art will appreciate that various changes can be made to these processes in attaining these and other advantages, without departing from the scope of the present disclosure. As such, it should be understood that the features of the disclosure are susceptible to modifications and/or substitutions without departing from the scope of this disclosure. The specific embodiments illustrated and described herein are for illustrative purposes only, and not limiting of the invention set forth in the appended claims.

ilizing converts at least a portion of the dextrose to DP2+ sugars; b) combining the heat sterilized fermentation medium with an enzyme capable of converting DP2+ sugars to dextrose, whereby at least a portion of the DP2+ sugars produced during heat sterilizing is converted to dextrose, thereby producing a modified heat sterilized fermentation medium comprising more dextrose and less DP2+ sugars than without combining the medium with the enzyme; and c) placing a microorganism in contact with the modified heat sterilized fermentation medium to produce a polyunsaturated fatty acid (PUFA), wherein the microorganism is capable of utilizing dextrose to produce the polyunsaturated fatty acid (PUFA).

2. The process of claim 1, wherein the microorganism is not capable of utilizing DP2+ sugars to produce the polyunsaturated fatty acid (PUFA).

3. The process of claim 1, wherein the enzyme is an alpha-glucosidase enzyme.

4. The process of claim 1, wherein the enzyme is derived from *Trichoderma reesei* expressing an alpha glucosidase from *Aspergillus niger*.

5. The process of claim 1, wherein the polyunsaturated fatty acid (PUFA) is omega-3 fatty acid or docosahexaenoic acid (DHA).

6. The process of claim 1, further comprising converting the polyunsaturated fatty acid (PUFA) to a fatty acid methyl ester (FAME).

| Experiment | Fermentor | EFT | DP2 | DP3 | Total Solids | DHA in FAME % | FAME in Biomass % | DHA in Biomass % | Whole Broth Titer g/l | DHA (g) | Fermenzyme volume (additive) (ml)* | Number of Enzyme Additions | Antifoam Usage (g) | Foam out (+/−) |
|---|---|---|---|---|---|---|---|---|---|---|---|---|---|---|
| Control Fermentations | | | | | | | | | | | | | | |
| DHA1505 | C2 | 72 | 8.04 | 3.43 | 275.5 | 37.8 | 58.9 | 22.2 | 62.2 | 323.75 | 0 | 0 | na | ++ |
| DHA1506 | C4 | 72 | 20.96 | 2.08 | 294.7 | 37.4 | 59 | 22.1 | 67.4 | 341.04 | 0 | 0 | na | + |
| DHA1509 | C1 | 72 | 18.26 | 2.31 | 264.1 | 38.5 | 57 | 21.9 | 59.5 | 306.43 | 0 | 0 | 14.5 | ++ |
| DHA1510 | C2 | 72 | 16.5 | 2.67 | 264.7 | 35.1 | 55.9 | 19.6 | 53.4 | 311.86 | 0 | 0 | 25.5 | ++ |
| DHA1511 | C4 | 72 | 18.37 | 2.92 | 281.5 | 35.8 | 55.1 | 19.7 | 57.4 | 320.87 | 0 | 0 | na | ++ |
| Ave at 72 hrs | | | 16.426 | 2.68 | 276.1 | 36.8 | 57.2 | 21.1 | 60 | 320.8 | | | 20 | 1.8 |
| Sd | | | | | 12.7 | 1.4 | 1.8 | 1.3 | 5.2 | 13.3 | | | | |
| Test Fermentations | | | | | | | | | | | | | | |
| DHA1505 | C3 | 72 | 3.44 | 1.54 | 258.4 | 38.6 | 61.2 | 23.6 | 62 | 364.9 | 4.2 | 3 adds | na | + |
| DHA1506 | C2 | 72 | 2.48 | 0.9 | 287.7 | 38.2 | 61.2 | 23.4 | 69.2 | 377.8 | 4.5 | 1 adds | na | ++ |
| DHA1506 | C3 | 72 | 4.22 | 1.87 | 256.3 | 38.9 | 59.8 | 23.3 | 60.9 | 329.5 | 4.5 | 1 adds | na | − |
| DHA1509 | C2 | 72 | 4.19 | 2.13 | 240 | 35.6 | 60.7 | 21.6 | 53 | 318 | 4.5 | 1 adds | 14.5 | + |
| DHA1509 | C3 | 72 | 4.37 | 2.37 | 238.5 | 36.3 | 59.7 | 21.7 | 52.9 | 311.5 | 4.5 | 1 adds | 13.5 | − |
| DHA1509 | C4 | 72 | 3.72 | 1.68 | 262.2 | 36 | 60.8 | 21.9 | 58.9 | 337.5 | 4.5 | 3 adds | 13.5 | ++ |
| DHA1510 | C1 | 72 | 3.29 | 1.21 | 247.8 | 36.1 | 61.4 | 22.1 | 56.5 | 314.7 | 4.5 | 3 adds | 13.5 | − |
| DHA1510 | C3 | 72 | 3.69 | 1.84 | 248.2 | 36.1 | 61.2 | 22.1 | 56.5 | 336.2 | 4.5 | 1 adds | 15 | + |
| DHA1510 | C4 | 72 | 3.47 | 1.45 | 253.7 | 35.6 | 59.8 | 21.3 | 55.7 | 309.1 | 4.5 | 1 adds | 21.5 | + |
| DHA1511 | C1 | 72 | 1.21 | 1.44 | 270.3 | 36 | 59.3 | 21.4 | 59.3 | 370.6 | 4.5 | 1 adds | na | + |
| DHA1511 | C2 | 72 | 2.17 | 0.95 | 273.8 | 35.1 | 59.4 | 20.8 | 58.7 | 328.7 | 4.5 | 1 adds | na | + |
| DHA1511 | C3 | 72 | 1.56 | 0.63 | 263.4 | 36.3 | 60.8 | 22.1 | 59.5 | 367.7 | 4.5 | 3 adds | na | − |
| Ave at 72 hrs | | | 3.15 | 1.5 | 258.4 | 36.6 | 60.4 | 22.1 | 58.6 | 338.9 | | | 15.8 | 0.83 |
| Sd | | | | | 14.3 | 1.3 | 0.8 | 0.9 | 4.4 | 25 | | | | |

Foam out:
<500 ml
500-999 ml +
1000-1499 ml ++
>1500 ml +++

What is claimed is:

1. A process of fermenting comprising: a) heat sterilizing a fermentation medium comprising dextrose to produce a heat sterilized fermentation medium, wherein the heat ster- 7. The process of claim 1, wherein the microorganism is of algal origin.

8. The process of claim 1, wherein the microorganism is a Schizochytrium sp.

9. The process of claim 1, wherein the placing a microorganism in contact with the modified heat sterilized fermentation medium, wherein the microorganism is capable of utilizing dextrose, but not DP2+ sugars, to produce an omega-3 fatty acid.

10. The process of claim 1, wherein the heat sterilizing converts at least a portion of the dextrose to DP2 and DP3 sugars.

11. The process of claim 1, wherein the step of placing the microorganism in contact with the modified heat sterilized fermentation medium produces a product having more polyunsaturated fatty acid (PUFA) and less residual sugar than a product produced by placing the microorganism in contact with the heat sterilized fermentation medium produced in step a).

12. The process of claim 1, wherein the step of placing the microorganism in contact with the modified heat sterilized fermentation medium produces a product having more polyunsaturated fatty acid (PUFA) and less total solids than a product produced by placing the microorganism in contact with the heat sterilized fermentation medium produced in step a).

13. The process of claim 1, wherein the step of placing the microorganism in contact with the modified heat sterilized fermentation medium produces a product having more polyunsaturated fatty acid (PUFA) and less foam than a product produced by placing the microorganism in contact with the heat sterilized fermentation medium produced in step a).

14. The process of claim 1, wherein the step of placing the microorganism in contact with the modified heat sterilized fermentation medium produces a product having more polyunsaturated fatty acid (PUFA) and that dries easier than a product produced by placing the microorganism in contact with the heat sterilized fermentation medium produced in step a).

15. The process of claim 1, wherein the step of placing the microorganism in contact with the modified heat sterilized fermentation medium produces a product having more polyunsaturated fatty acid (PUFA) and that has less stickiness upon drying than a product produced by placing the microorganism in contact with the heat sterilized fermentation medium produced in step a).

16. The process of claim 1, wherein the step of placing the microorganism in contact with the modified heat sterilized fermentation medium produces a product having more polyunsaturated fatty acid (PUFA) and less caramelized residual sugar than a product produced by placing the microorganism in contact with the heat sterilized fermentation medium produced in step a).

17. The process of claim 1, wherein the enzyme is diluted 1:1 with deionized water and sterile filtered prior to step b).

18. The process of claim 1, wherein the enzyme is injected into a fermenter in one to three aliquots at one to three different points in time, with the first point in time being earlier in fermentation and distinct from the other points in time.

* * * * *